(12) United States Patent
Van et al.

(10) Patent No.: US 7,368,240 B2
(45) Date of Patent: May 6, 2008

(54) MICROSCOPE SYSTEM AND METHODS FOR INTRACELLULAR STUDIES

(75) Inventors: Sang Van, San Diego, CA (US); Lei Yu, Carlsbad, CA (US)

(73) Assignee: Nitto Denko Corporation, Ibaraki, Osaka (JP)

( * ) Notice: Subject to any disclaimer, the term of this patent is extended or adjusted under 35 U.S.C. 154(b) by 447 days.

(21) Appl. No.: 10/980,079

(22) Filed: Nov. 3, 2004

(65) Prior Publication Data

US 2005/0112667 A1 May 26, 2005

Related U.S. Application Data

(60) Provisional application No. 60/519,019, filed on Nov. 11, 2003.

(51) Int. Cl.
*C12Q 1/68* (2006.01)
(52) U.S. Cl. .......................... 435/6; 435/455; 435/468; 435/471

(58) Field of Classification Search .................. None
See application file for complete search history.

(56) References Cited

U.S. PATENT DOCUMENTS

| 5,902,246 A | * | 5/1999 | McHenry et al. | ........... 600/476 |
| 5,919,445 A | * | 7/1999 | Chao | ......................... 424/93.2 |
| 2005/0265978 A1 | * | 12/2005 | Chancellor et al. | ........ 424/93.7 |

* cited by examiner

*Primary Examiner*—James S Ketter
(74) *Attorney, Agent, or Firm*—Knobbe, Martens, Olson & Bear, LLP

(57) ABSTRACT

A microscope system, kit and method are described for observation of cellular activity in real time. The system is used to monitor cell transfection using a polynucleotide noncovalently attached to a carrier, The carrier labeled with a dye or fluorescent agent so that transport of complex can be monitored in real time. The polynucleotide includes both a gene of interest and a reporter gene. The reporter gene indicates successful expression of the gene of interest.

19 Claims, 5 Drawing Sheets

Red Green Phase Phase + Fluorescence

Time    3:55 pm (Red)    3:55 pm (Green)    3:55 pm (Phase)

Time    4:13 pm (Red)    4:13 pm (Green)    4:13 pm (Phase)

MICROSCOPE SYSTEM AND METHODS FOR INTRACELLULAR STUDIES

RELATED APPLICATIONS

This application claims priority of U.S. Provisional application No. 60/519,019, filed Nov. 11, 2003 which is incorporated herein by reference.

BACKGROUND OF THE INVENTION

1. Field of the Invention

This invention relates generally to technology useful for in vitro polynucleotide delivery applications. In one aspect, methods for monitoring intracellular activity in real time are disclosed. More particularly, this invention relates to polynucleotides and labeled gene carriers which monitor transport within cells and gene expression using a fluorescence microscope equipped with a mercury lamp, objective lenses, excitation filter, and a high resolution digital camera. The technology is useful for in vitro delivery applications in mammals.

2. Description of the Related Art

There is a need for non-viral drug and gene delivery systems having desirable properties such as low immunogenicity, amenable to production on a relatively large scale, and which can be easily modified to provide a range of biological properties. See Mulligan, R. C. Science 260, 926-932 (1993); and Luo, et al. Nat. Biotechnol. 18, 33-37 (2000). A number of polycationic polymers and lipids have facilitated plasmid DNA transfection of cells. See Kircheis et al. Adv. Drug Deliver. Rev. 2001, 53, 341-358. It is believed that polymer-DNA complexes enter cells by an endocytotic pathway as illustrated in FIG. 1.

It is generally recognized that there are four barriers to transport of a biomolecule, such as a gene, into the cell. These are the cell membrane, endosome membrane, nuclear membrane and the release of the biomolecule from the carrier. In the case of a nucleic acid, the nucleic acid-carrier complex must first pass through the cell membrane (path 1, FIG. 1). When this is accomplished by endocytosis, the nucleic acid-carrier complex is then internalized. The carrier along with the nucleic acid-cargo is enveloped by the cell membrane by the formation of a pocket and the pocket is subsequently pinched off (path 2, FIG. 1). The result is a cell endosome, which is a large membrane-bound structure enclosing the nucleic acid cargo, and the carrier. The nucleic acid-carrier complex must then escape from the endosome membrane into the cytoplasm (path 4, FIG. 1), avoid enzyme degradation in the cytoplasm, and cross the nuclear membrane (path 5, FIG. 1). Once in the nucleus, the nucleic acid cargo must separate from the carrier. In general, anything designed to overcome one or more of the barriers described above may be considered a delivery enhancer.

In general, delivery enhancers fall into two categories. These are viral carrier systems and non-viral carrier systems. As human viruses have evolved ways to overcome the barriers to transport into the nucleus discussed above, viruses or viral components are useful in transport of nucleic acid into cells. One example of a viral component useful as a delivery enhancer is the hemagglutinin peptide (HA-peptide). This viral peptide facilitates transfer of biomolecules into cells by endosome disruption. At the acidic pH of the endosome, this protein causes release of the biomolecule and carrier into the cytosol.

Non-viral delivery enhancers may be either polymer-based or lipid-based. They are generally polycations which act to balance the negative charge of the nucleic acid. Polycationic polymers have shown significant promise as non-viral gene delivery enhancers due in part to their ability to condense DNA plasmids of unlimited size and to safety concerns with viral vectors. Examples include peptides with regions rich in basic amino acids such as oligo-lysine, oligo-arginine or a combination thereof and polyethylenimine (PEI). These polycationic polymers facilitate transport by condensation of DNA. Branched chain versions of polycations such as PEI and Starburst dendrimers can mediate both DNA condensation and endosome release (Boussif, et al. (1995) Proc. Natl. Acad. Sci USA vol. 92: 7297-7301). PEI is a highly branched polymer with terminal amines that are ionizable at pH 6.9 and internal amines that are ionizable at pH 3.9 and because of this organization, can generate a change in vesicle pH that leads to vesicle swelling and eventually, release from endosome entrapment.

Another means to enhance delivery is to design a ligand on the carrier. The ligand must have a receptor on the cell that has been targeted for cargo delivery. Biomolecule delivery into the cell is then initiated by receptor recognition. When the ligand binds to its specific cell receptor, endocytosis is stimulated. Examples of ligands which have been used with various cell types to enhance biomolecule transport are galactose, transferrin, the glycoprotein asialoorosomucoid, adenovirus fiber, malaria circumsporozite protein, epidermal growth factor, human papilloma virus capsid, fibroblast growth factor and folic acid. In the case of the folate receptor, the bound ligand is internalized through a process termed potocytosis, where the receptor binds the ligand, the surrounding membrane closes off from the cell surface, and the internalized material then passes through the vesicular membrane into the cytoplasm (Gottschalk, et al. (1994) Gene Ther 1:185-191).

Various agents have been used for endosome disruption. Besides the HA-protein described above, defective-virus particles have also been used as endosomolytic agents (Cotten, et al. (July 1992) Proc. Natl. Acad. Sci. USA vol. 89: pages 6094-6098). Non-viral agents are either amphiphillic or lipid-based.

The release of biomolecules such as DNA into the cytoplasm of the cell can be enhanced by agents that either mediate endosome disruption, decrease degradation, or bypass this process all together. Chloroquine, which raises the endosomal pH, has been used to decrease the degradation of endocytosed material by inhibiting lysosomal hydrolytic enzymes (Wagner, et al. (1990) Proc Natl Acad Sci USA vol. 87: 3410-3414). Branched chain polycations such as PEI and starburst dendrimers also promote endosome release as discussed above.

To completely bypass endosomal degradation, subunits of toxins such as Diptheria toxin and *Pseudomonas* exotoxin have been utilized as components of chimeric proteins that can be incorporated into a gene/gene carrier complex (Uherek, et al. (1998) J. Biol. Chem. vol. 273: 8835-8841). These components promote shuttling of the nucleic acid through the endosomal membrane and back through the endoplasmic reticulum.

Once in the cytoplasm, the nucleic acid cargo must find its way to the nucleus. Localization to the nucleus may be enhanced by inclusion of a nuclear localization signal on the nucleic acid-carrier. A specific amino acid sequence that functions as a nuclear-localization signal (NLS) is used. The NLS on a cargo-carrier complex interacts with a specific nuclear transport receptor protein located in the cytosol. Once the cargo-carrier complex is assembled, the receptor protein in the complex is thought to make multiple contacts with nucleoporins, thereby transporting the complex through a nuclear pore. After a cargo-carrier complex reaches its destination, it dissociates, freeing the cargo and other components.

Technology that provides visualization of dynamic behaviors (paths 1-6, FIG. 1) of the complexes inside cells has been limited. Some workers have used electron microscopy to investigate the visualization of complexes inside cells. See Joshee et al. Human Gene Therapy 2002, 13, 1991-2004; and Panyam et al. Int. J. Pharm. 262, 1-11 (2003). However, this method does not allow the study of the dynamic behavior of living cells. Other workers have used confocal microscopy to study intracellular trafficking, but the system is expensive and observation could not be longer than 30 minutes. See Godbey, et al. PNAS 96, 5177-5181 (1999). Fluorescence microscopy has been used to observe a whole cell, but resolution inside the cell was poor. See Mathew et al. Gene Therapy, 10, 1105-1115 (2003).

In order to develop effective transfection reagents, there is a need for technology and methods to detect and monitor gene-DNA complexes inside cells. In this patent application, we disclosed technology and methods to monitor the real-time visualization and dynamic behavior inside cells.

SUMMARY OF THE INVENTION

Embodiments of the invention are directed to a method of monitoring cell transport activity in real time which includes the steps of 1) transfecting cells with a composition where the composition contains at least one polynucleotide encoding a gene of interest and a reporter gene, and a labeled carrier attached to the polynucleotide; 2) monitoring the cell transport activity in real time with a microscope system by observation of the label; and 3) monitoring expression of the reporter gene. Preferably, the dye or fluorescent compound indicates transport of the nucleotide into the cell nucleus and the reporter gene indicates expression of the gene of interest.

In preferred embodiments, the polynucleotide is circular DNA, linear DNA, PCR products, DNA oligos, linear RNA, siRNA, RNAi, or Ribozyme. In some preferred embodiments, the gene of interest is the reporter gene. In preferred embodiments, the polynucleotide includes both the gene of interest and the reporter gene in tandem. In alternate preferred embodiments, the gene of interest and the reporter gene are on separate polynucleotides attached to the carrier. In preferred embodiments, the reporter gene encodes a GFP. Preferably, the cell transport activity is gene transfection.

Preferably, the carrier is a viral vector, a lipid based carrier, a polymer based carrier, a lipid-polymer based carrier, a polysaccharide based carrier, a protein or peptide based carrier, or a metal ions based carrier.

Preferably, the label is selected from Alexa Fluor dyes, BODIPY dyes. Cascade blue dyes, coumarin, Digoxigenin, Environment-Sensitive dyes, Fluorescein, FITC, Haptens, Lissamine Rhodamine B dyes, NBD, Oregon Green dyes, Blue-Fluorescent dyes, photosensitizers, QSY Fluorescent-Dye quenchers, Rhodamine 6G dyes, Rhodamine green dyes, Rhodamine red dyes, tetramethylrhodamine, and Texas red dyes.

In preferred embodiments, the carrier is noncovalently attached to the polynucleotide. In alternate preferred embodiments, the carrier is covalently attached to the polynucleotide. In some preferred embodiments, the carrier also includes a nuclear localization signal.

Preferably, the cell is a mammalian cell, an insect cell or a plant cell.

Preferably, the microscope system includes a fluorescence microscope, a mercury lamp, objective lenses, excitation filter and high resolution digital camera.

Embodiments of the invention are directed to a kit for monitoring DNA transfection which includes a transfection vector with a reporter gene and an insertion site for a gene of interest; and a labeled carrier to which the transfection vector can be attached. Preferably, the reporter gene encodes a GFP. Preferably, the carrier is a viral vector, a lipid based carrier, a polymer based carrier, a lipid-polymer based carrier, a polysaccharide based carrier, a protein or peptide based carrier, or a metal ions based carrier.

Preferably, the label is selected from Alexa Fluor dyes, BODIPY dyes, Cascade blue dyes, coumarin, Digoxigenin, Environment-Sensitive dyes, Fluorescein, FITC, Haptens, Lissamine Rhodamine B dyes, NBD, Oregon Green dyes, Blue-Fluorescent dyes, photosensitizers, QSY Fluorescent-Dye quenchers, Rhodamine 6G dyes, Rhodamine green dyes, Rhodamine red dyes, tetramethylrhodamine, and Texas red dyes.

In some preferred embodiments, the gene of interest is the reporter gene. In some preferred embodiments, the polynucleotide includes both the gene of interest and the reporter gene in tandem. In some preferred embodiments, the gene of interest and the reporter gene are on separate polynucleotides.

In some preferred embodiments, the carrier is noncovalently attached to the polynucleotide. In some preferred embodiments, the carrier is covalently attached to the polynucleotide. In some preferred embodiments, the carrier also includes a nuclear localization signal.

Embodiments of the invention are directed to a system for monitoring cellular activity in real time which includes the kit described above and a fluorescence microscope. In preferred embodiments, the microscope includes a mercury lamp, objective lenses, excitation filter, and a high resolution digital camera. Preferably, the objective lens is 40-63× with N.A. 1.4. More preferably, the objective lens further also includes a 1.6× or 2.0× magnification. Preferably, the system also includes a laser system.

Embodiments of the invention are directed to a method of monitoring a transfection experiment which includes transfecting a cell with a transfection vector which expresses a reporter gene complexed with a carrier labeled with a dye or fluorescent compound; monitoring the carrier; and monitoring the expression of the reporter gene.

Preferably, the reporter gene encodes a GFP. Preferably, the cell is a mammalian cell, an insect cell or a plant cell.

In preferred embodiments, the carrier is a viral vector, a lipid based carrier, a polymer based carrier, a lipid-polymer based carrier, a polysaccharide based carrier, a protein or peptide based carrier, or a metal ions based carrier.

Preferably, the dye or fluorescent compound is selected from Alexa Fluor dyes, BODIPY dyes, Cascade blue dyes, coumarin, Digoxigenin, Environment-Sensitive dyes, Fluorescein, FITC, Haptens, Lissamine Rhodamine B dyes, NBD, Oregon Green dyes, Blue-Fluorescent dyes, photosensitizers, QSY Fluorescent-Dye quenchers, Rhodamine 6G dyes, Rhodamine green dyes, Rhodamine red dyes, tetramethylrhodamine, and Texas red dyes.

DETAILED DESCRIPTION OF THE PREFERRED EMBODIMENT

Figure 1:
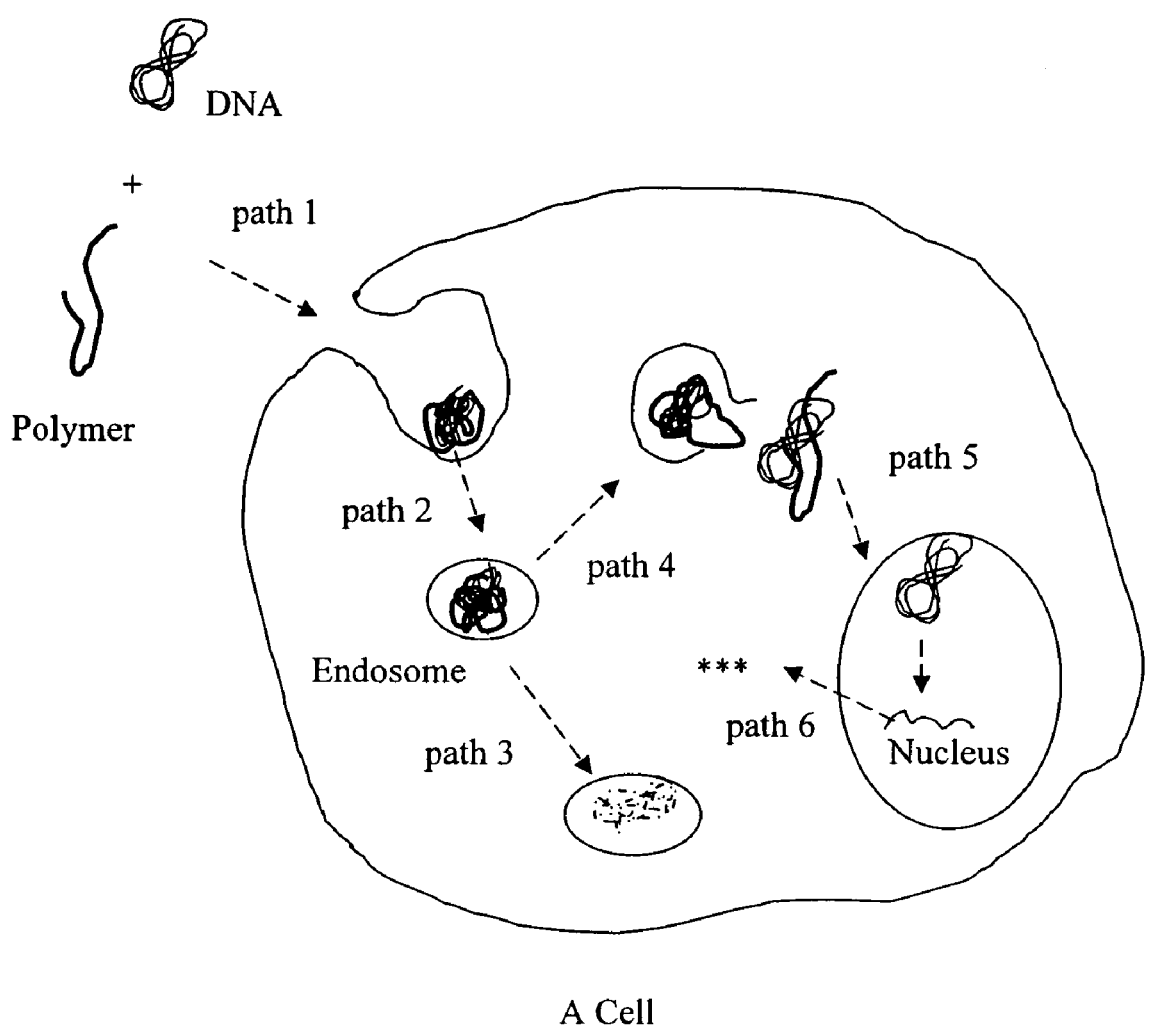
FIG. 1 illustrates an endocytotic pathway for the entry of a polymer-DNA complex into a cell. Path 1 indicates the complexation of polymer and DNA. Path 2 indicates internalization via endocytosis. Path 3 leads to a lysosome. Path 4 indicates endosome escape. Path 5 indicates nucleus internalization. Path 6 leads to gene expression.
Figure 2:
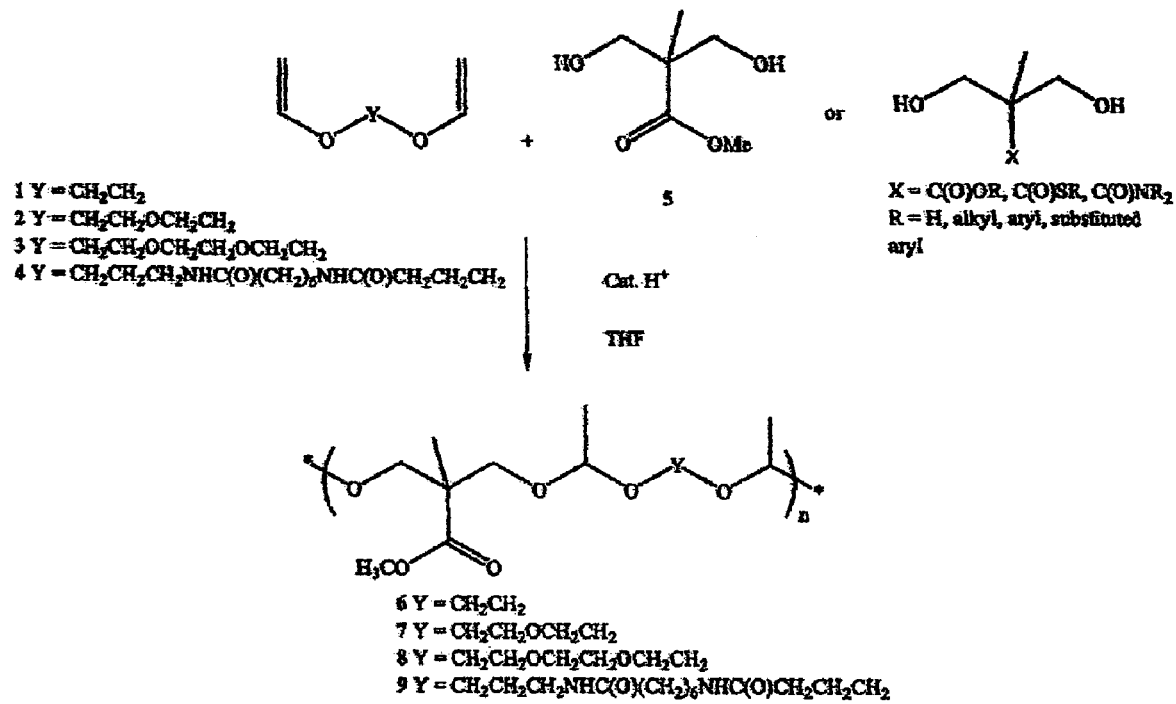
FIG. 2 shows a preferred reaction scheme for the synthesis of polyacetals 6-9.
Figure 3:
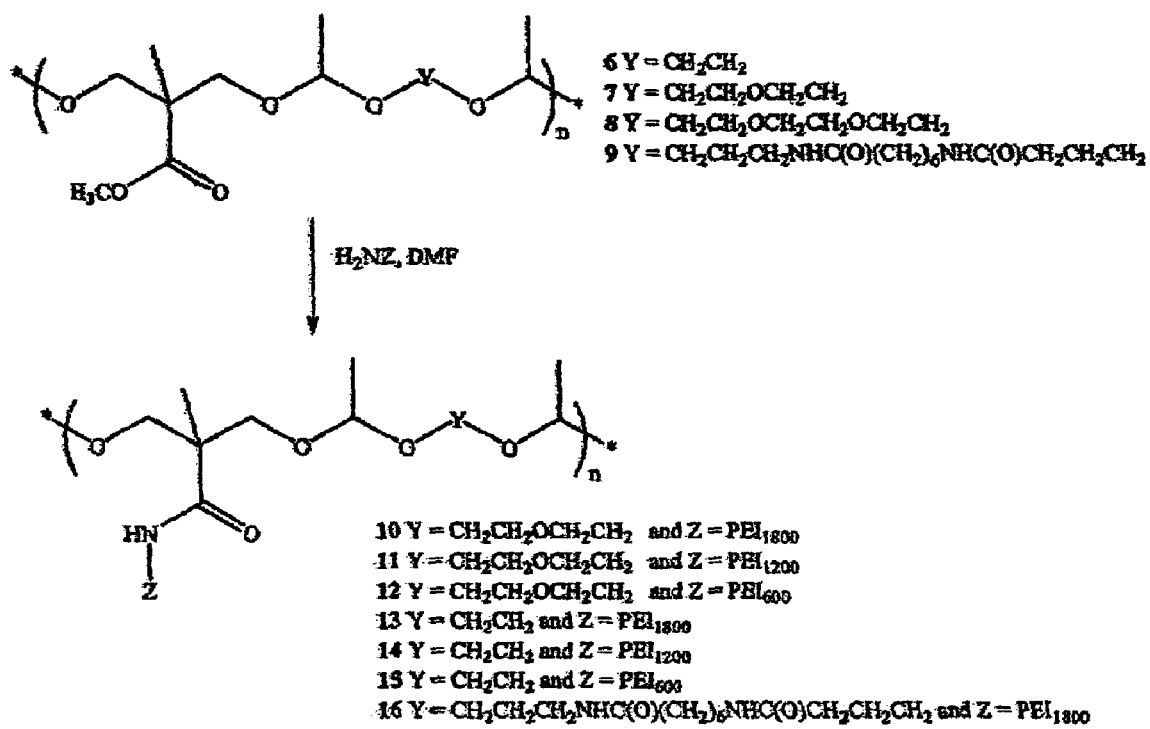
FIG. 3 shows a preferred reaction scheme for the synthesis of polyacetals 10-16.

In one aspect the present invention combines imaging technology with gene delivery technology to provide real-time visualization of the dynamic behavior of polymer-DNA complexes inside cells for a reasonable cost. The described method may also be used to monitor cellular trafficking and complex formation intra- and intercellularly. In a preferred embodiment, a nucleotide to be transported is covalently or noncovalently attached to a labeled carrier which is monitored in a cell using a microscope. In preferred embodiments, the label is a dye or fluorescent compound. In most preferred embodiments, the carrier is fluorescently labeled and the microscope is a fluorescence microscope.

In preferred embodiments, the nucleotide includes a gene of interest and a reporter gene. In some embodiments, the gene of interest is the reporter gene. The gene of interest and the reporter may be tandemly linked on the same polynucleotide or they may be on separate polynucleotides independently attached to the labeled carrier. For example, the gene of interest and the reporter gene may be on separate vectors independently attached to the labeled carrier. More preferably, the gene of interest and the reporter gene are on the same vector or polynucleotide.

In preferred embodiments, molecules of interest include but are not limited to DNA and RNA, particularly circular DNA, linear DNA, PCR products, DNA oligos, linear RNA, siRNA, RNAi, and Ribozymes. While preferred embodiments are directed to nucleotides, the intracellular movement of other molecules of interest may also be monitored using the methods and kits described herein. In particular protein transport may be monitored with an appropriate carrier, labeled with a dye or fluorescent compound.

Preferably, the reporter gene encodes one or more Green Fluorescent Proteins (GFP).

The carrier compound is labeled with a dye or fluorescent label. Preferred labeling compounds include the fluorescent labels Alexa Fluor dyes, BODIPY dyes, Cascade blue dyes, coumarin, Digoxigenin, Environment-Sensitive dyes, Fluorescein, FITC, Haptens, Lissamine Rhodamine B dyes, NBD, Oregon Green dyes, Blue-Fluorescent dyes, photosensitizers, QSY Fluorescent-Dye quenchers, Rhodamine 6G dyes, Rhodamine green dyes, Rhodamine red dyes, tetramethylrhodamine, and Texas red dyes. In most preferred embodiments, the fluorescent label is FITC-Fluorescence-5-X or rhodamine red.

Preferably the labeled carrier is a viral vector, polycationic or cationic lipid based carrier, polycationic or cationic polymer based carrier, polycationic or cationic lipid-polymer based carrier, polycationic or cationic polysaccharide based carrier, polycationic or cationic protein or peptide based carrier, or metal ions based. Preferably, the nucleotide or other molecule of interest is noncovalently attached to the fluorescently labeled carrier. In a preferred embodiment, the carrier is a polycationic polymer such as polyethylenimine or polyacetal.

Polyacetals are polymers that contain acetal (—O—CHR—O—) recurring units. Preferred polyacetals comprise recurring units represented by formula (I):

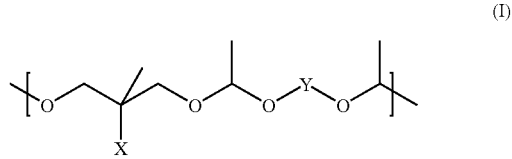

In formula (I), X is preferably selected from the group consisting of $C(O)OR^1$, $C(O)SR^1$, $C(O)NR^1R^2$, and VZ, where $R^1$ and $R^2$ are each individually selected from the group consisting of hydrogen, $C_1$ to $C_{10}$ alkyl, and $C_6$ to $C_{10}$ aryl, and where V is a linker group. In this context, "a linker group" is a bifunctional chemical group that joins one chemical group to another. Linker groups can contain a single bifunctional chemical group such as amide, or may contain two chemical groups such as amide-amide, amide-alkyl, alkyl-amide, amine-amide, or thioether-amide. Examples of preferred linker groups include —C(O)NH—, —C(O)NH—$R^1$—C(O)NH—, —C(O)NH—$R^1$—, —$R^1$—C(O)NH—, —NH—$R^1$—C(O)NH—, —S—$R^1$—C(O)NH, where $R^1$ is selected from the group consisting of hydrogen, $C_1$ to $C_{10}$ alkyl, and $C_6$ to $C_{10}$ aryl.

In formula (I), Z is preferably selected from the group consisting of poly(ethyleneimine) (PEI), poly(propyleneimine) (PPI), poly(lysine), polyamidoamine (PAMAM) dendrimers, octaamine dendrimers, and hexadecaamine dendrimers. PEI and PPI, if used, preferably have a molecular weight in the range of about 200 to about 100,000 Daltons. Poly(lysine), if used, preferably has a molecular weight in the range of about 200 to about 50,000 Daltons. In formula (I), Y is preferably selected from the group consisting of —$(CH_2)_2$—, —$(CH_2)_2$—O—$(CH_2)_2$—, —$(CH_2)_2$—O—$(CH_2)_2$—O—$(CH_2)_2$—, and —$(CH_2)_3$—NHC(O)—$(CH_2)_6$—C(O)NH—$(CH_2)_3$—.

Polyacetals may be copolymers and thus may contain two or more different recurring units represented by the formula (I), and/or other recurring units. A "polyacetal of the formula (I)" or "polymer of the formula (I)", as those terms are used herein, includes such copolymers as well as homopolymers consisting essentially of recurring units of the formula (I). In a preferred embodiment, a polyacetal comprises a recurring unit of the formula (II):

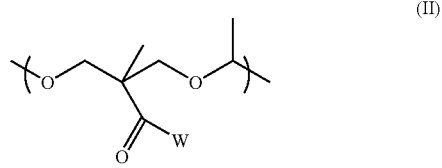

In formula (II), W is preferably selected from the group consisting of an enhancer and a targeting receptor. In this context, an "enhancer" is a functional group that is capable of enhancing the efficiency of gene transfection to a eukaryotic cell and a "targeting receptor" is a functional group that is capable of recognizing specific receptors on a cell surface. The foregoing definitions are not mutually exclusive, and thus W may be both an enhancer and a targeting receptor. Preferably, W is selected from the group consisting of lipid, cholesterol, transferrin, antibody, antibody fragment, galactose, mannose, lipoprotein, lysosomotrophic agent, and fusogenic agent. A "polyacetal of the formula (II)" or "polymer of the formula (II)", as those terms are used herein, includes copolymers comprising a recurring unit of the formula (II) as well as homopolymers consisting essentially of recurring units of the formula (II). A preferred polyacetal comprises a recurring unit of the formula (I) and a recurring unit of the formula (II).

Enhancers and/or a targeting receptors may be attached to polyacetals in various ways, e.g., by covalent bonding to the polyacetal as shown in formula (II), by conjugating an enhancer and/or a targeting receptor to Z in formula (I), or both. For example, in a preferred embodiment, a polyacetal comprises a recurring unit of the formula (I) and a recurring unit of the formula (II) in which X in formula (I) is VZ. The Z group in formula (II) may be conjugated to W (in which case the enhancer and/or a targeting receptor represented by W is attached to the polyacetal in at least two places, via conjugation to Z and covalent attachment to the recurring unit represented by the formula II), and/or the Z group in formula (II) may be conjugated to a second enhancer and/or second targeting receptor. Thus, two or more enhancers and/or a targeting receptors may be attached to a polyacetal.

Various methods may be used to make polyacetals. A preferred method comprises reacting a diol represented by the formula (III) with a divinyl ether represented by the formula (IV):

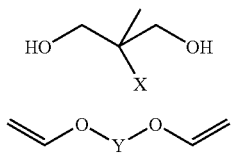

(III)

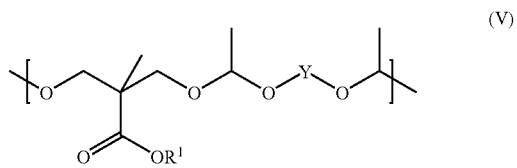

(IV)

In formulae (III) and (IV), X and Y have the same meanings as set forth above. The polymerization reaction is preferably conducted by intermixing a diol represented by the formula (III) with a divinyl ether represented by the formula (IV) in a polar aprotic solvent such as tetrahydrofuran in the presence of an acid catalyst such as p-toluenesulfonic acid (pTSA). Optionally, the mixture may contain one or more other diols and/or divinyl ethers. Preferably, the mole ratio of diol(s) to divinyl ether(s) in the mixture is approximately 1:1, although the exact ratio may be varied to adjust the molecular weight of the resulting polymer. Higher molecular weights are generally achieved when the ratio is closer to 1:1. Lower molecular weights may be achieved by using a slight excess of either the diol(s) or the divinyl ethers, and/or by including small amounts of monofunctional alcohols and/or vinyl ethers. Preferably, the molecular weights of the resulting polyacetal (e.g., a polymer or copolymer comprising a recurring unit represented by the formulae (1) and/or (2)) are about 1,000 Daltons or greater, more preferably in the range of about 1,000 to about 250,000 Daltons.

Recurring units represented by the formula (I) encompass two genera, one in which X is selected from the group consisting of $C(O)OR^1$, $C(O)SR^1$, and $C(O)NR^1R^2$, and the other in which X is VZ. Polyacetals in which X is selected from the group consisting of $C(O)OR^1$, $C(O)SR^1$, and $C(O)NR^1R^2$ are useful for making polyacetals in which X is VZ. For example, polyacetals comprising a recurring unit of the formula (I) in which X is VZ and V is —C(O)NH— are preferably made by reacting a compound represented by the formula $H_2NZ$ with a polyacetal comprising a recurring unit of the formula (I) in which X is $C(O)OR^1$, as shown in formula (V):

(V)

In formula (V), $R^1$ and Y have the same meanings as set forth above. For the compound represented by the formula $H_2NZ$, Z has the same meaning as set forth above. The reaction of the compound represented by the formula $H_2NZ$ with the polyacetal of the formula (V) is preferably conducted in a polar solvent such as dimethylformamide. The polyacetal of the formula (V) may be prepared by reacting a diol of the formula (III) in which X is —C(O)OR^1 with a divinyl ether of the formula (IV), under the general conditions described above for the polymerization of diols and divinyl ethers. A "polyacetal of the formula (V)" or "polymer of the formula (V)", as those terms are used herein, includes copolymers comprising a recurring unit of the formula (V) as well as homopolymers consisting essentially of recurring units of the formula (V).

It has been found that polyacetals of the formula (I) in which X is VZ form complexes with polynucleotides such as DNA and RNA. Thus, another embodiment provides a complex comprising a polyacetal of the formula (I) and a polynucleotide, in which the X in the polyacetal of the formula (I) is VZ, where V and Z have the same meanings as set forth above. Preferably, V is —C(O)NH—. Such complexes are preferably formed by intermixing the polyacetal of the formula (I) (in which X is VZ) and a polynucleotide. Preferably, such intermixing is conducted by adding a solution containing the polyacetal to a second solution containing the polynucleotide. Complexation may be verified by examining the retardation of the polynucleotide-polyacetal band on agarose gel electrophoresis.

It has been found that complexes comprising polyacetals of the formula (I) (in which X is VZ) and polynucleotides are useful for transfecting cells. Transfection is preferably conducted by contacting the cell with the complex. It has been found that preferred complexes comprising polymers of the formula (I) (in which X is VZ) and polynucleotides are relatively non-toxic.

The cells of the invention are preferably eukaryotic cells including but not limited to mammalian cells, insect cells, and plant cells. In preferred embodiments, the cells of the invention are 293, COS-7, huvec cells, neuron primary cells, and undifferentiated NT-2 cells.

The detection system is preferably a fluorescent microscope system. Preferably, the fluorescence microscope is equipped with a laser system as an emission light source and carbon dioxide incubator to visualize the interaction of fluorescent labeled carrier noncovalently attached to genetic materials within cell compartments and intracellular pathways. Preferably, the microscope system includes one or more of the following components: a mercury lamp, a high resolution digital camera, filter sets, 63× objective lenses with Numerical Aperture (N.A.) 1.4, and 1.6× or 2.0× optivar additional magnification. In one particular most preferred embodiment, the microscope system includes an inverted microscope, such as the Zeiss axiovert S 100 microscope.

In a preferred embodiment, gene carriers labeled with fluorescent compounds are used in transfection experiments. The genetic materials may be any types of DNA or RNA including but not limited to circular DNA, linear DNA, PCR products, DNA oligos, linear RNA, siRNA, RNAi, or Ribozyme. The progress of the transfection is monitored using a fluorescence microscope.

Simply, we have developed technology that can follow gene-polymer complexes within cells. This invention was designed for real-time visualization and dynamic behavior of the DNA-polymer complexes inside cells. The invention will have significant impact on design of gene carriers.

EXAMPLES

Gene carriers were synthesized according to the procedure in U.S. application Ser. No. 10/375,075, filed Feb. 25, 2003, which is incorporated herein by reference and described below, or purchased from Polysciences, Inc. FITC-Fluorescence-5-X and Rhodamine Red were purchased from Molecular Probes. The conjugation of fluorescent dye to gene carriers was performed by the literature's procedure (Godbey, et al. PNAS 96, 5177-5181 (1999)).

A Zeiss axiovert S100 microscope and a Quantix Q-57 backthinned, cooled CCD camera were used. The Rhodamine was imaged with a Chromatechnologies 41002 filter set. The FITC-Fluorescence-5-X and the GFP were imaged with Achroma technologies 41028 filter set optimized for Yellow Fluorescent Proteins (YFP) but suitable for said excitation and emission. A 40× oil immersion, NA 1.4, objective and either a 1.6× or 2.0× optivar additional magnification were used.

Cell lines and cultures used in the following examples were prepared as follows: Kangaroo kidney cells ("PTK2 cells") were purchased from American Type Culture Collection, Manassas, Va., and grown in Dulbecco's-modified Eagle's medium (DMEM) containing 10% (v/v) heat-inactivated fetal bovine serum (FBS), 100 U/ml Penicillin and 100 µg/ml streptomycin, and incubated at 37° C. at 100% humidity atmosphere containing 7.5% $CO_2$.

GFP plasmids used in the following examples were prepared as follows: Plasmid pCMV-GFP was purchased from Clontech (Palo Alto, Calif.). The expression of green fluorescent protein (GFP) cDNA was controlled by the human cytomegalovirus (CMV) promoter and the transcripts were stabilized by a gene expression enhancer, chicken β-globulin intron. The plasmid was expanded in DHR5α *E. coli* and purified with a Plasmid Maxi Kit (obtained commercially from Qiagen, Valencia, Calif.) according to the manufacturer's instructions. The quantity and quality of the purified plasmid DNA was assessed by spectrophotometric analysis at 260 and 280 nm as well as by electrophoresis in 0.8% agarose gel. Purified plasmid DNA was resuspended in sterile distilled, deionized $H_2O$ and frozen.

Examples 1-4

The following description for the synthesis of polyacetal is illustrative: Di(ethylene glycol) divinyl ether (1.39 g, 8.76 mmol) and bis-(2-hydroxymethyl)methyl propionate (1.30 g, 8.76 mmol) were mixed in tetrahydrofuran (THF) (10 mL) with molecular sieves (1.0 g) at room temperature and stirred for 20 min. A catalytic amount of toluensulfonic acid monohydrate (TSA, 0.015 g, 0.08 mmol) was added and stirring was continued for four days. The reaction mixture was quenched with sodium bicarbonate (1 mL, 5% in water) or triethylamine (1 mL). Water (10 mL) was added and the organic phase was extracted with ethylacetate (3×10 mL). The extracts were combined, dried with sodium sulfate, filtered, and concentrated by rotary evaporation. The residue was dried under high vacuum to give polyacetal (2.65 g, 8.65 mmol, 98%) as an oil.

Examples 5-11

The following description for the synthesis of polyacetal is illustrative: To poly(ethylenimine) ($PEI_{1800}$) (30 g, 16.7 mmol) was added a solution of polyacetal (0.5 g, 1.63 mmol) in dimethylformamide (DMF) (10 mL). Additional DMF (10 mL) was added and the mixture was stirred for four days. THF (100 mL) was added to form a precipitate. The precipitate was filtered and washed with THF, then dried under high vacuum to give polyacetal (2.2 g).

Example 12

A polyacetal-poly(ethylenimine) conjugated with an enhancer was prepared as follows:

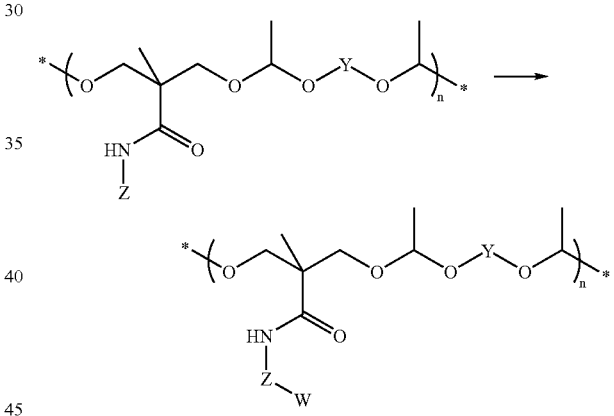

10 Y = $CH_2CH_2OCH_2CH_2$ and Z = $PEI_{1800}$
17 Y = $CH_2CH_2OCH_2CH_2$, Z = $PEI_{1800}$, and W = cholesterol Polyacetal 10 (0.55 g) and dimethylsulfoxide (DMSO) (50 mL) were combined in a vial. Cholesteryl chloroformate (1.0 g) and triethylamine (1 mL) were added and the resulting mixture was stirred for 20 minutes, filtered to remove an insoluble residue, and washed with dichloromethane (30 mL). The resulting solid residue was dried under high vacuum to give 1.3 grams of polyacetal 17.

Example 13

DNA/Polymer Complex Formation

Fresh Modified Essential Medium (OPTI-MEM, 1550 µL) was placed in one well of a six well plate (allocate at least 3-wells per sample) for the preparation of the gene carrier prepared as described in Example 1. A solution of freshly prepared gene carrier polymer, labeled with dye (rhodamine) and/or fluorescence (FITC-X) (52 µL of a 10 mg/mL solution in PBS) was added to the OPTI-MEM well and mixed thoroughly. Fresh OPTI-MEM (1000 µL) was placed in a separate well for diluting the plasmid DNA. A DNA solution (20 µL, 1 µg/µL) was added to the well and mixed thoroughly. The DNA solution (240 µL) and the gene carrier polymer solution (240 µL) were placed in another separate well and mixed by pipeting several times. The ratio of polymer to DNA (by weight) was 16:1. The mixture was allowed to equilibrate for 15 min at room temperature.

Figure 4:
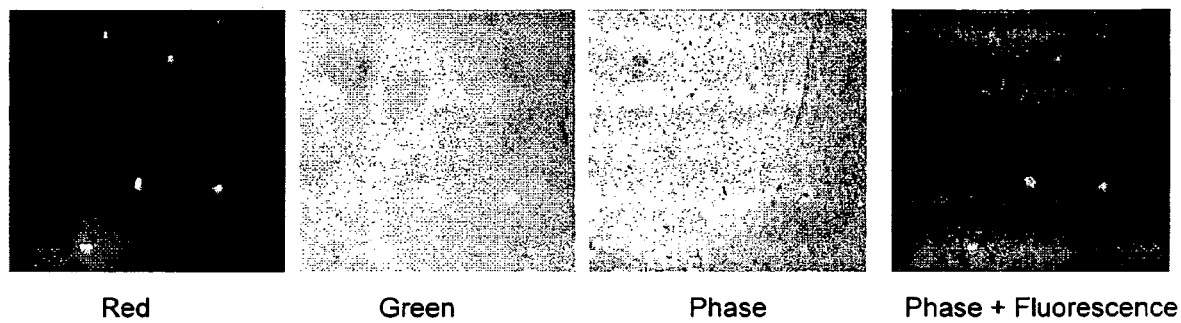
FIG. 4 shows a reproduction of photographs of images of DNA-polymer labeling complexes within a cell. Labeling: Red=Red wavelengths on only, Green=Green wavelengths on only, Phase=white light only, Phase+Fluorescence=white light and red wavelengths.
Figure 5:
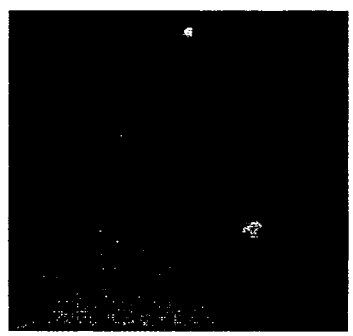
FIG. 5 shows a reproduction of photographs of images of DNA-polymer labeling complexes within a cell at two time points.
Figure 5:
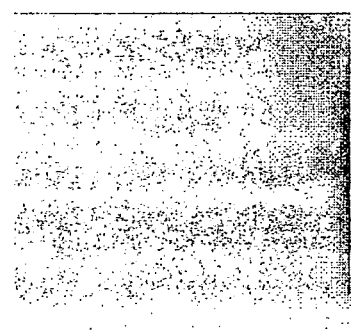
Figure 5:
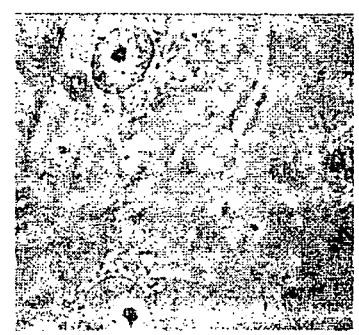
Figure 5:
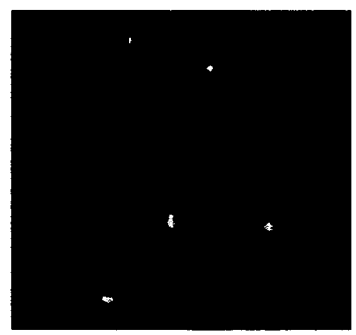
Figure 5:
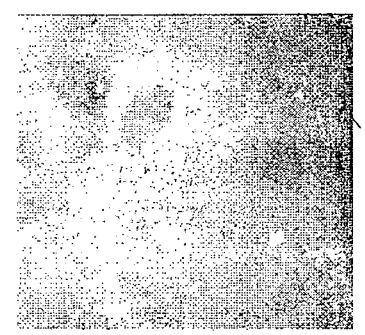
Figure 5:
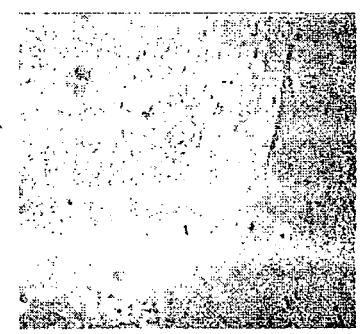

Complex Interaction with the Cells:

A chamber containing cells in desired cell confluency was examined for cell condition (isolated healthy cells). The DNA/Polymer complex (240 µL) was injected into the chamber with a thin needle and syringe (21 gauge) with another needle at the opposite end of the chamber to release extra fluid pressure and air. The injected chamber was equilibrated at room temperature for 15 min. The chamber was flushed with fresh OPTI-MEM (6 ml) to reduce background florescence if necessary and was placed under a fluorescent microscope system for observation. The images were captured with a high resolution digital camera for an appropriate period of time (FIGS. 4 & 5). Images (FIG. 4) were captured inside a kangaroo "PTK2" cell using red wavelength and green wavelength emission as well as white light (phase) and phase+fluorescence (FIG. 4, from left to right, respectively). The dynamic and visualization of gene carrier-DNA complexes was monitored in real-time. The cross-section of z-axis can be also monitored to cover visualization at various depths within the cell. GFP was also observed after 20 hours post-transfection.

FIG. 5 shows PTK2 cells at two different time points monitored with red wavelength and green wavelength emission and white light (phase). Similar results have been obtained using Alexa dye as a label (not shown).

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of monitoring cell transport activity in real time comprising:
    transfecting cells with a composition comprising:
        at least one polynucleotide encoding a gene of interest and a reporter gene; and
        a labeled carrier attached to the polynucleotide;
    monitoring the cell transport activity in real time with a microscope system by observation of the label; and
    monitoring expression of the reporter gene,
wherein the label on the labeled carrier is a dye or fluorescent compound which indicates transport of the nucleotide into the cell nucleus and wherein the reporter gene indicates expression of the gene of interest.

2. The method of claim 1, wherein the polynucleotide is selected from the group consisting of circular DNA, linear DNA, PCR products, DNA oligos, linear RNA, siRNA, RNAi, and Ribozyme.

3. The method of claim 1, wherein the gene of interest is the reporter gene.

4. The method of claim 1, wherein the polynucleotide comprises both the gene of interest and the reporter gene in tandem.

5. The method of claim 1, wherein the gene of interest and the reporter gene are on separate polynucleotides attached to the carrier.

6. The method of claim 1, wherein the reporter gene encodes a GFP.

7. The method of claim 1, wherein the cell transport activity is gene transfection.

8. The method of claim 1, wherein the carrier is selected from the group consisting of a viral vector, a lipid based carrier, a polymer based carrier, a lipid-polymer based carrier, a polysaccharide based carrier, a protein or peptide based carrier, and a metal ions based carrier.

9. The method of claim 1, wherein the label is selected from the group consisting of Alexa Fluor dyes, BODIPY dyes, Cascade blue dyes, coumarin, Digoxigenin, Environment-Sensitive dyes, Fluorescein, FITC, Haptens, Lissamine Rhodamine B dyes, NBD, Oregon Green dyes, Blue-Fluorescent dyes, photosensitizers, QSY Fluorescent-Dye quenchers, Rhodamine 6G dyes, Rhodamine green dyes, Rhodamine red dyes, tetramethylrhodamine, and Texas red dyes.

10. The method of claim 1, wherein the carrier is noncovalently attached to the polynucleotide.

11. The method of claim 1, wherein the carrier is covalently attached to the polynucleotide.

12. The method of claim 1, wherein the carrier further comprises a nuclear localization signal.

13. The method of claim 1, wherein the cell is a mammalian cell, an insect cell or a plant cell.

14. The method of claim 1, wherein the microscope system comprises a fluorescence microscope, a mercury lamp, objective lenses, excitation filter and high resolution digital camera.

15. A method of monitoring a transfection experiment comprising:
    transfecting a cell with a transfection vector which expresses a reporter gene complexed with a carrier labeled with a dye or fluorescent compound;
    monitoring the carrier; and
    monitoring the expression of the reporter gene.

16. The method of claim 15, wherein the reporter gene encodes a GFP.

17. The method of claim 15, wherein the cell is selected from the group consisting of a mammalian cell, an insect cell and a plant cell.

18. The method of claim 15, wherein the carrier is selected from the group consisting of a viral vector, a lipid based carrier, a polymer based carrier, a lipid-polymer based carrier, a polysaccharide based carrier, a protein or peptide based carrier, and a metal ions based carrier.

19. The method of claim 15, wherein the dye or fluorescent compound is selected from the group consisting of Alexa Fluor dyes, BODIPY dyes, Cascade blue dyes, coumarin, Digoxigenin, Environment-Sensitive dyes, Fluorescein, FITC, Haptens, Lissamine Rhodamine B dyes, NBD, Oregon Green dyes, Blue-Fluorescent dyes, photosensitizers, QSY Fluorescent-Dye quenchers, Rhodamine 6G dyes, Rhodamine green dyes, Rhodamine red dyes, tetramethylrhodamine, and Texas red dyes.

* * * * *

UNITED STATES PATENT AND TRADEMARK OFFICE
CERTIFICATE OF CORRECTION

| | | |
|---|---|---|
| PATENT NO. | : 7,368,240 B2 | Page 1 of 1 |
| APPLICATION NO. | : 10/980079 | |
| DATED | : May 6, 2008 | |
| INVENTOR(S) | : Van et al. | |

It is certified that error appears in the above-identified patent and that said Letters Patent is hereby corrected as shown below:

On the Title Page, Item (57), Abstract, Line 4, "to a carrier, The carrier labeled" should be changed to --to a carrier. The carrier is labeled--

Column 1, Lines 31-32, "See Kircheiset al." should be changed to --See Kircheis et al.--

Column 2, Line 52, "as Diptheria toxin" should be changed to --as Diphtheria toxin--

Column 9, Line 54, "expanded in DHR5α" should be changed to --expanded in DH5α--

Column 11, Line 6, "mixed by pipeting" should be changed to --mixed by pipetting--

Signed and Sealed this

Twenty-first Day of October, 2008

JON W. DUDAS
*Director of the United States Patent and Trademark Office*